(12) United States Patent
Ancel et al.

(10) Patent No.: US 6,479,703 B1
(45) Date of Patent: Nov. 12, 2002

(54) METHOD FOR PREPARING POLYHALOGENATED PARATRIFLUOROMETHYLANILINES

(75) Inventors: Jean-Erick Ancel, Saint-Genis-Laval; Eliane Darnand, Lyons, both of (FR)

(73) Assignee: Aventis CropScience SA (FR)

( * ) Notice: Subject to any disclaimer, the term of this patent is extended or adjusted under 35 U.S.C. 154(b) by 0 days.

(21) Appl. No.: 09/868,349

(22) PCT Filed: Dec. 10, 1999

(86) PCT No.: PCT/FR99/03090

§ 371 (c)(1),
(2), (4) Date: Aug. 23, 2001

(87) PCT Pub. No.: WO00/35851

PCT Pub. Date: Jun. 22, 2000

(30) Foreign Application Priority Data

Dec. 17, 1998 (FR) .............................. 98 16164

(51) Int. Cl.⁷ .............................. C07C 209/00
(52) U.S. Cl. ...................................... 564/405
(58) Field of Search ......................... 564/405

(56) References Cited

U.S. PATENT DOCUMENTS

| | | | |
|---|---|---|---|
| 4,096,185 A | | 6/1978 | Seiwell |
| 4,197,259 A | | 4/1980 | Guzik |
| 4,952,601 A | * | 8/1990 | Wolleber et al. |
| 5,300,692 A | | 4/1994 | Sakamoto et al. |

FOREIGN PATENT DOCUMENTS

| | | |
|---|---|---|
| CA | 1241665 | 9/1988 |
| DE | 292238 A5 | 7/1991 |
| EP | 0315869 | 5/1989 |
| JP | 5255206 | 10/1993 |

* cited by examiner

*Primary Examiner*—Samuel Barts
(74) *Attorney, Agent, or Firm*—Ostrolenk, Faber, Gerb & Soffen, LLP

(57) ABSTRACT

The invention concerns a novel method for preparing polyhalogenated paratrifluormethylanilines particularly useful as reaction intermediates for preparing compositions used as insecticides. The products of the inventive method are obtained by the action of ammonia on polyhalogenated para-trifluoromethylbenzene at a temperature ranging between 150 and 350° C. The inventive reaction can be carried out in the presence of an alkaline halide.

20 Claims, No Drawings

METHOD FOR PREPARING POLYHALOGENATED PARATRIFLUOROMETHYLANILINES

This application is a 371 of PCT/FR99/03090 filed Dec. 10, 1999.

DESCRIPTION

The subject-matter of the present invention is a novel process for the preparation of polyhalogenated para-trifluoromethylanilines, more particularly of dihalo-para-trifluoromethylanilines.

Processes making possible the preparation of anilines substituted by a halogen atom have formed the subject of many studies and of numerous patents or publications.

Thus, the subject-matter of U.S. Pat. No. 4,096,185 is a process for the amination of halogenated aromatic compounds, such as para-trifluoromethylaniline, from para-chloro-trifluoromethylbenzene and with the use of a specific catalytic combination targeted at improving the yield of the reaction.

The process of U.S. Pat. No. 4,197,259 discloses the preparation of monohalogenated anilines by the use of difficult reaction conditions related to the use of an alkali metal amide as aminating agent; this is because, as the use of such an alkali metal amide requires the reaction to be carried out in the absence of any trace of water in the react on mixture, these reaction conditions render fairly problematic the implementation of such a process on an industrial scale; in addition, such reaction conditions involve significant difficulties related to the dissipation of the heat of reaction.

East German Patent 292,238 relates to the preparation of nitrated and monohalogenated anilines.

European Patent Application 173,202 discloses the preparation of 5-chloro-2-nitroanilines.

Japanese Patent 5 255,206 and European Patent Application 543,633 have, as subject-matter, the preparation of monofluoroanilines and or monofluorinated trifluoromethylanilines respectively.

Thus, despite the large number of studies carried out to develop novel synthetic routes, in particular for the purpose of improving the known processes for the preparation of halogenated anilines, virtually all the methods known to date only relate to monohalogenated anilines alone.

In addition, and although Japanese Patent 7 025,834 has disclosed a process for the preparation of polyhalogenated nitroanilines, it is often impossible to apply these reactions to compounds substituted by a trifluoromezhyl group due, inter alia, to the low reactivity conferred on the reactants by this trifluoromethyl group.

One of the aims of the present invention is to provide a method for the preparation of polyhalogenated para-trifluoromethylanilines.

Another aim of the invention is to solve the problems related to the preparation of 2,6-dihalogenated and 4-trifluoromethylated anilines while avoiding the formation of polyamination products and products from the hydrogenation of the aromatic residue.

An additional aim of the process of the invention is to promote the formation of polyhalogenated para-trifluoromethylanilines instead of meta-trifluoromethylated isomers.

It has now been found that these objectives can be achieved in all or part by virtue of the process according to the invention.

It is a process for the preparation of polyhalogenated derivatives of trifluoromethylaniline by reaction [lacuna] polyhalogenated trifluoromethylbenzenes, particularly of 3,4,5-trihalo-trifluoromethylbenzenes, for example of 4-bromo-3,5-dichloro-trifluoromethylbenzene or of 3,4,5-trichloro-trifluoromethylbenzene, with ammonia.

The reaction of the process according to the invention is carried out at a temperature of between 150 and 350° C., more particularly between 180 and 270° C., and advantageously in a polar organic solvent.

The reaction of the invention can, in addition to ammonia, be carried out in the presence of an alkali metal halide.

Thus, the process according to the invention makes possible the preparation of the products of formula (I):

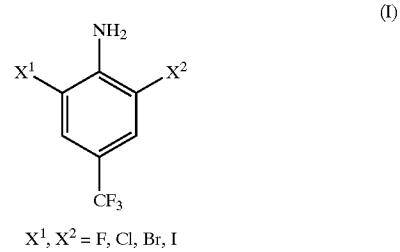

$X^1, X^2 = F, Cl, Br, I$ from reactants of formula (II):

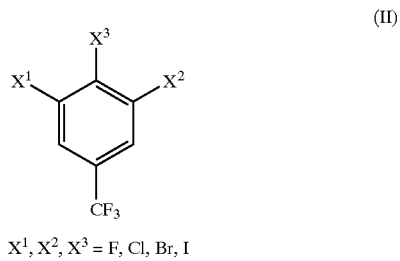

$X^1, X^2, X^3 = F, Cl, Br, I$

When it is present, the alkali metal halide is present in a catalytic amount, particularly in an amount of between 1 and 50% of the amount of reactant of formula (II) used, more particularly in an amount of between 5 and 20%. The alkali metal halide is advantageously an alkali metal fluoride or bromide, preferably a lithium halide.

The process according to the invention is advantageously carried out with a content of water in the reaction mixture such that the $H_2O/NH_3$ ratio is less than 80/100, preferably less than 20/100, more preferably less than 2/100.

The organic solvent optionally employed in the invention is preferably a polar organic solvent, more preferably a nonionic polar organic solvent, for example an N-alkylpyrrolidone, the alkyl radical of which preferably has from 1 to 12 carbon atoms. The use of N-methylpyrrolidone is preferred.

The pressure which prevails in the mixture during the reaction according to the invention is an autogenous pressure resulting from the use of a closed system, for example an autoclave, in order to exert the best control over the amount of ammonia present.

The product resulting from the reaction according to the invention is separated from the reaction mixture by any conventional means, for example by distillation, by extraction or by extraction followed by distillation, or by isolation of salts obtained by the action of hydrochloric acid.

For the purpose of isolating the aniline derivative obtained, the unreacted polyhalogenated para-trifluoromethylbenzene is separated from the reaction mixture. In the case where only a small amount of the benzene derivative used is present, this stage can be omitted.

By carrying out the reaction of the process according to the invention in a reactor equipped with a distillation apparatus, the targeted aniline derivative and the unreacted benzene derivative are directly separated from the reaction mixture by distillation.

In order to isolate the targeted reaction product by extraction, water and an organic solvent of low boiling point, for example ether, dichloromethane or hexane, are added to the reaction mixture. After separation of the aqueous phase, the organic phase is distilled in order to separate the targeted aniline derivative from the unreacted benzene derivative. The benzene derivative, thus separated, is then recycled as reactant for the process of the invention.

Another method of separation of the reaction product of the invention is its salification by the action of hydrochloric acid. For this, the reaction mixture is diluted in a solvent in which the targeted salified aniline derivative has little solubility and hydrochloric acid is subsequently run into the reaction mixture in order to precipitate the targeted aniline derivative thus salified. The precipitate obtained is subsequently filtered off.

The process of the invention makes possible the preparation of the envisaged aniline derivatives with a particularly advantageous degree of conversion of the reactants. The performance of the process of the invention varies, however, depending on the specific reaction conditions chosen; a person skilled in the art can easily find optimum reaction conditions by using the information given in the present description.

Another advantage of the process of the invention is to allow the conversion of polyhalogenated trifluoromethylbenzenes to aniline derivatives with a high yield.

This process is also particularly advantageous in that it is highly selective, promoting the formation of polyhalogenated para-trifluoromethylanilines rather than polyhalogenated meta-trifluoromethylanilines.

An additional advantage of the process of the invention is that it makes possible reaction times which can be short; for example, reaction times of less than 10 hours, indeed even reaction times of less than 5 hours, can be employed.

The polyhalogenated trifluoromethylanilines which can be prepared by the process according to the invention include 2,6-dichloro-4-trifluoromethylaniline, which is particularly advantageous as a reaction intermediate in the preparation of compounds used as insecticides.

The various examples which follow will make it possible to more fully illustrate the process of the invention and the advantages which are attached thereto; however, these examples do not in any way limit the scope of the invention.

EXAMPLE NO. 1

3,4,5-Trichloro-trifluoromethylbenzene (0.681 g, 2.73 mmol), lithium fluoride (7.1 mg, 0.273 mmol) and N-methylpyrrolidone (1.8 ml) are mixed in an autoclave. The autoclave is cooled to −95° C. and then ammonia (1.3 g, 76.4 mmol) is added. The autoclave is then heated at 250° C. and with stirring for 4 h and is subsequently allowed to return to room temperature. The reaction product is extracted by washing with water and with dichloromethane and then the organic phase is evaporated, after having been dried. 0.453 g (1.97 mmol) of 2,6-dichloro-4-trifluoromethylaniline is obtained with a degree of conversion of the 3,4,5-trichloro-trifluoromethylbenzene of 97%, a ratio equal to 83/17 for the selectivity for 2,6-dlchloro-para-trifluoromethylaniline with respect to 2,6-dichloro-meta-trifluoromethylaniline and an 87% yield of 2,6-dichloro-para-trifluoromethylaniline.

EXAMPLE NO. 2

4-Bromo-3,5-dichloro-trifluoromethylbenzene (0.802 g, 2.73 mmol) and N-methylpyrrolidone (1.8 ml) are mixed in an autoclave. The autoclave is cooled to −95° C. and then ammonia (1.3 g, 76.4 mmol) is added. The autoclave is then heated at 200° C. and with stirring for 4 h and is subsequently allowed to return to room temperature.

The reaction product is extracted by washing with water and with dichloromethane and then the organic phase is evaporated, after having been dried.

0.428 g (1.86 mmol) of 2,6-dichloro-4-trifluoromethylaniline is obtained with a degree of conversion of the 4-bromo-3,5-dichloro-trifluoromethybenzene of 91%, complete selectivity for 2,6-dichloro-para-trifluoromethylaniline and a 68% yield of 2,6-dichloro-para-trifluoromethylaniline.

What is claimed is:

1. Process for the preparation of products of formula (I):

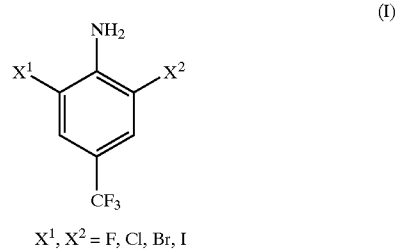

$X^1, X^2 = F, Cl, Br, I$ comprising reacting a reactant of formula (II):

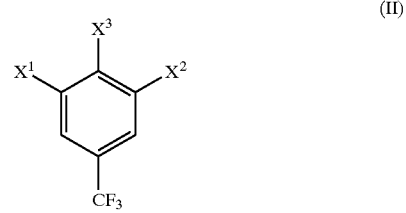

$X^1, X^2, X^3 = F, Cl, Br, I$ with ammonia at a temperature of between 180 and 350° C.

2. Process according to claim 1 effected in the presence of an alkali metal halide.

3. Process according to claim 2, in which the alkali metal halide is present in a catalytic amount.

4. Process according to claim 2, in which the alkali metal halide is present in an mount of between 1 and 50% of the molar amount of reactant of formula (II).

5. Process according to claim 1, in which the content of water in the reaction mixture is such that the $H_2O/NH_3$ ratio is less than 80/100.

6. Process according to claim 1, in which a polar organic solvent.

7. Process according to claim 6, in which the solvent employed is an N-alkylpyrrolidone.

8. Process according to claim 1 in which the temperature is 180–270° C.

9. Process according to claim 2 in which the temperature is 180–270° C.

10. Process according to claim 4 in which the alkali metal halide is present in an amount between 5 and 20% of the molar amount of reactant to formula (II).

11. Process according to claim 5 in which the $H_2O/NH_3$ ratio is less than 20:100.

12. Process according to claim 5 in which the $H_2O/NH_3$ ratio is less than 2:100.

13. Process according to claim 6 in which the polar-organic solvent is nonionic.

14. Process according to claim 7 in which the alkyl-radical of the N-alkylpyrrolidone has 1–12 carbon atoms.

15. Process according to claim 7 in which the N-alkylpyrrolidone is N-methylpyrrolidone.

16. Process according to claim 1 in which the content of water of the reaction mixture is such that the $H_2O/NH_3$ is less than 80:100 and in which polar organic solvent is used.

17. Process according to claim 3 in which the alkali metal halide is present in an amount between 5 and 20% of the molar amount of reactant formula (II), the content of water in the reaction mixture is such that the $H_2O/NH_3$ ratio is less than 80:1 and in which a polar organic solvent is used.

18. Process according to claim 17 in which the $H_2O/NH_3$ ratio is less than 20/100, the polar organic solvent is non-ionic and the temperature is between 180 and 270° C.

19. Process according to claim 18 in which the $H_2O/NH_3$ ratio is less than 2/100 and the organic solvent is an N-alkylpyrrolidone.

20. Process according to claim 19 in which the N-alkylpyrrolidone is N-methylpyrrolidone and in which the alkali metal halide is a lithium halide.

* * * * *